US007814906B2

(12) United States Patent
Moretti

(10) Patent No.: US 7,814,906 B2
(45) Date of Patent: Oct. 19, 2010

(54) METHOD AND RELEVANT APPARATUS FOR NASAL VENTILATION, PARTICULARLY FOR FLOW-SYNCHRONISED NEONATAL ASSISTED VENTILATION

(75) Inventor: Corrado Moretti, Cecchina (IT)

(73) Assignee: Ginevri S.r.l., Cecchina (RM) (IT)

( * ) Notice: Subject to any disclaimer, the term of this patent is extended or adjusted under 35 U.S.C. 154(b) by 1081 days.

(21) Appl. No.: 11/418,196

(22) Filed: May 5, 2006

(65) Prior Publication Data
US 2006/0249156 A1 Nov. 9, 2006

(30) Foreign Application Priority Data
May 6, 2005 (IT) .......................... RM2005A0217

(51) Int. Cl.
*F16K 31/02* (2006.01)
*A61M 16/00* (2006.01)

(52) U.S. Cl. ............................. 128/204.23; 128/204.21; 128/204.18

(58) Field of Classification Search .................
128/200.24–200.26, 204.18, 204.21–204.23, 128/204.26, 204.29–205.12, 207.16, 207.18
See application file for complete search history.

(56) References Cited

U.S. PATENT DOCUMENTS

| 4,323,064 | A  | * | 4/1982 | Hoenig et al. | .......... 128/204.21 |
| 5,953,713 | A  | * | 9/1999 | Behbehani et al. | ............ 706/16 |
| 6,626,175 | B2 | * | 9/2003 | Jafari et al. | ............ 128/204.21 |
| 6,739,335 | B1 |   | 5/2004 | Rapport et al. | |
| 2003/0145852 | A1 | * | 8/2003 | Schmidt et al. | ........ 128/203.12 |
| 2003/0145856 | A1 | * | 8/2003 | Zdrojkowski et al. | .. 128/204.18 |
| 2003/0172929 | A1 | * | 9/2003 | Muellner | ................ 128/204.18 |
| 2004/0112381 | A1 | * | 6/2004 | Ujhazy et al. | .......... 128/204.18 |
| 2004/0221848 | A1 | * | 11/2004 | Hill | ........................ 128/204.18 |
| 2007/0163590 | A1 | * | 7/2007 | Bassin | .................... 128/204.23 |

FOREIGN PATENT DOCUMENTS

| DE | 101 18 968 | 10/2002 |
| WO | WO 92/11054 | 7/1992 |
| WO | WO 02/18002 | 3/2002 |

* cited by examiner

*Primary Examiner*—Justine R Yu
*Assistant Examiner*—Rachel T Young
(74) *Attorney, Agent, or Firm*—Young & Thompson

(57) ABSTRACT

In a method for nasal ventilation and relevant apparatus, particularly for flow-synchronized neonatal assisted ventilation, wherein F(t) is a signal proportional to the ventilation flow, the following steps are performed:
(a) inspiration, having a time length Ti, during which air is introduced at an inspiration pressure;
(b) expiration, having a time length Te, during which the introduction of air is interrupted;
(c) return to step (a);
with a flow threshold Ftr, during the expiration step (b) the following steps are provided:
(b1) a waiting step having a time length γ before activation of computation of the leakages; and
(b2) a step of leakage computation, having a time length δ, so that γ+δ=Te, wherein if a normalized signal F' (t), obtained by a processing by way of an algorithm of the surveyed signal F(t), exceeds the threshold Ftr, a spontaneous respiration activity is detected and the inspiration step (a) is reactivated.

21 Claims, 4 Drawing Sheets

METHOD AND RELEVANT APPARATUS FOR NASAL VENTILATION, PARTICULARLY FOR FLOW-SYNCHRONISED NEONATAL ASSISTED VENTILATION

FIELD OF THE INVENTION

The present invention relates to a method and relevant apparatus for nasal ventilation, particularly for flow-synchronised neonatal assisted ventilation.

More specifically, the invention concerns a method of the above kind, studied and realised particularly for permitting low weight newborn mechanical ventilation (partus immaturus) by a respiratory prosthesis comprised of two nasal cannulae (nose-cannulae) thus avoiding, when possible, tracheal intubation.

BACKGROUND OF THE INVENTION

As it is well known, low weight premature new-borns require many therapeutic interventions aimed to stabilise and ensure their main vital functions, particularly respiration.

In fact, respiratory insufficiency is the most frequent reason of morbidity and mortality of these young patients.

Treatment of medium-serious level respiratory insufficiency in premature new-borns is realised sustaining the spontaneous respiratory activity of the patient by the use of an automatic ventilator, apparatus able to deliver intermittent positive pressures (+10, +25 cm $H_2O$), with an air and oxygen flow with variable concentration (Intermittent positive Pressure Ventilation: IPPV).

Respirator is provided with a specific ventilation circuit and connection between said circuit and the patient respiratory system is realised by a tube of suitable material and dimensions. Said tube is then fixed in such a way that its distal end is positioned within tertius medius of infant trachea. Thus, a closed pneumatic system is created, permitting transmission of pressure waves generated by the respirator at the patient respiratory system.

In the last decade, clinical research has clearly demonstrated that, among the main factors of the pathogenesis of acute and chronical lesions of a still developing respiratory system of these patients, it is necessary considering included:

1. lack of synchronism between mechanical cycles delivered by the respirator and the patient spontaneous respiratory activity (e.g. coincidence of mechanical inspiration and spontaneous expiration, with high pressures within the respiratory system).

2. prolonged presence of the tracheal tube since it creates lesions and infections.

These two problems have been separately solved by the development of synchronised ventilation (Synchronised IPPV: SIPPV) and of the not-invasive ventilation, realised using nose cannulae in place of tracheal tube (Nasal IPPV: NIPPV).

SIPPV has been realised by the insertion of a small pneumotachograph between ventilation circuit and tracheal tube, i.e. an instrument able sensing inspiration flow caused by the spontaneous respiratory activity of the patient. Flow signal, as soon as intercepted, electronically determines the instantaneous activation of a mechanical cycle of the respirator (trigger system).

Application of this solution to the ventilation using nose-cannulae has not been possible until today, since presence of variable pressure leakages at the mouth (open or closed mouth) and nares level does not permit the use of flow signal for activation of trigger system. In fact, signal is unstable and with a too variable intensity to be suitably used by the trigger system presently known in the art.

On the other hand, lack of synchronism during nasal ventilation, besides having the side effects already described for IPPV, mainly determines a high variability of the treatment efficiency. In fact, not existing any more a closed system between ventilation circuit and aerial vie (tracheal tube), pressure wave generated by respirator is transmitted at the pulmonary level only if delivered during the patient spontaneous inspiration step, when glottides (phonatory cords) is physiologically dilated for easing the aerial flow. Delivering of a pressure during the patient spontaneous expiration step causes outlet of gas from the mouth and its by-pass at the gastric level, with the possibility of a dangerous abdominal distension. In order to realise newborn not-invasive synchronised ventilation (nSIPPV) it has then been used an "abdominal capsule", instrument able detecting the increase of abdominal pressure following the diaphragm contraction, i.e. the main respiratory muscle. Said solution has soon presented remarkable limits due to the high number of false activations caused by spontaneous movements of patient not finalised to ventilation. This involves dangerous consequences, first of all the hyperventilation that can even cause cerebral damage in low weight new-borns.

SUMMARY OF THE INVENTION

Object of the present invention is therefore that of providing a method permitting using flow-synchronised ventilation with nose-cannula, for treatment of respiratory insufficiency in premature new-borns, said method permitting both differentiating flow signal determined by spontaneous flow from that determined by leakages, and providing a stable and uniform signal for ensuring a uniform operation every time.

A second object of the invention is that of permitting the adjustment of a plurality of parameters.

A third object of the present invention is that of permitting a possible spontaneous respiratory activity during each step of the assisted respiration.

Further object of the present invention is that of providing the instruments necessary to carrying out the above method, and the relevant apparatuses.

It is therefore specific object of the present invention a method for nasal ventilation and relevant apparatus, particularly for flow-synchronized neonatal assisted ventilation, wherein F(t) is a signal proportional to the ventilation flow, comprising the following steps:

(a) inspiration, having a time length Ti, during which air is introduced at an inspiration pressure;

(b) expiration, having a time length Te, during which the introduction of air is interrupted;

(c) return to step (a);

characterised in that it comprises a flow threshold Ftr, and in that during said expiration step (b) the following steps are provided:

(b1) a waiting step having a time length $\gamma$ before the activation of the computation of the leakages; and (b2) a step of computation of the leakages, having a time length $\delta$, so that $\gamma+\delta=Te$, wherein if a normalized signal F'(t), obtained by a processing by means of an algorithm of the surveyed signal F(t), exceeds the threshold Ftr, a spontaneous respiration activity is detected and the inspiration step (a) is reactivated.

Always according to the invention, said algorithm can provide the following sub-steps:

sampling of the F(t) signal;

calculation of the variable average M(t) for each sample for Ti+γ<t<Ti+Te;

calculation of F'(t) signal according to formula F'(t)=F(t)−M(t) (for each t value).

Still according to the invention, said variable average M(t) is calculated according to the following formula:

$$M(t) = \frac{\sum_{i=1}^{N} F_i(t)}{N}$$

$$per\ Ti + \gamma < t < Ti + Te.$$

Wherein i is the index numbering F(t) samples; N is the number of samples used for calculation of leakages (b2).

Furthermore, according to the invention, calculation of average can be carried out for each sample acquired during step (b2), inserting each time the new value acquired.

Preferably, according to the invention number N of said samples can be 16.

Always according to the invention, step (b2) can be divided into two further steps, during respectively α and β, so that δ=α+β:

a first further waiting step;

a second step for verifying presence of spontaneous activity, wherein if F'(t) passes threshold Ftr, inspiration step (a) is reactivated.

Advantageously, according to the invention said time interval γ can be included in the range between 0.20 and 0.25 seconds, preferably 0.20 seconds.

Still according to the invention, said time interval α can be included in the range between 0.20 and 0.25 seconds, preferably 0.20 seconds.

Always according to the invention, in said method, during step b(2), if signal F'(t) takes value Ftr (with Ti+γ+α<t<Ti+γ+δ), inspiration step (a) can be reactivated.

Furthermore, according to the invention, during step (b2), within time interval δ it is possible memorising pressure at the end of expiration, and at the end of step (a) it is possible memorising maximum value of inspiration pressure.

Preferably, according to the invention, said inspiration time interval Ti and/or said expiration time interval Te can be varied.

Furthermore, according to the invention, said Ftr threshold can be varied.

It is furthermore object of the present invention an apparatus for carrying out said method, characterised in that it comprises a processing and control unit, interface means, suitable to adjust operation parameters by a user, a circuit for nasal ventilation and an electrovalve for activation—deactivation of the inspiration step, said electrovalve being connected with said circuit for nasal respiration.

Always according to the invention, said nasal ventilation circuit can comprise a nose-cannula connected with a pneumotachograph, to which flow tubes and pressure detection tubes are connected.

Still according to the invention, said apparatus can comprise memorisation means and/or interface means, said interface means including a monitor.

Furthermore, according to the invention, said interface means can comprise a push-button panel.

Preferably, according to the invention, Aid interface means can comprise a plurality of knobs.

Always according to the invention, said interface means can comprise a plurality of optical and/or acoustic warning devices.

Still according to the invention, said parameters can comprise inspiration time Ti, expiration time Te, expiration flow threshold Ftr, and respiration frequency.

Advantageously, according to the invention, said apparatus can comprise means for adjustment of respiration mixture.

BRIEF DESCRIPTION OF THE DRAWINGS

The present invention will be now described, for illustrative but not limitative purposes, according to its preferred embodiments, with particular reference to the figures of the enclosed drawings, wherein.

DETAILED DESCRIPTION OF EMBODIMENTS

In order to better understand the present invention, operation mode of the preferred embodiment of the inventive method will be described in the following, the same mode being valid also for other embodiments.

Procedure according to the present invention provides a particular sub-procedure permitting calculating leakages during assisted ventilation through nose-cannulae. This permits having an indication of effective flow arriving to new-born or patient, and thus to conform control trigger to the same flow.

Basic hypothesis on which the above procedure is based is existence of a physiological time interval, between the end of expiration and the beginning of a new inspiration, during which patient has no flow exchange with outside.

Main problem when carrying out said calculation is impossibility of exactly defining the end of suction, since ventilation circuit is open.

In order to overcome this problem it has been experimentally verified that since the ventilation circuit is an open circuit, and considering that said ventilation system is applied to new-borns, flow required by the patient within about 0.2 seconds from the end of the inspiration step can be considered negligible with respect to the circuit leakages (end of the effective suction step).

Figure 1A:
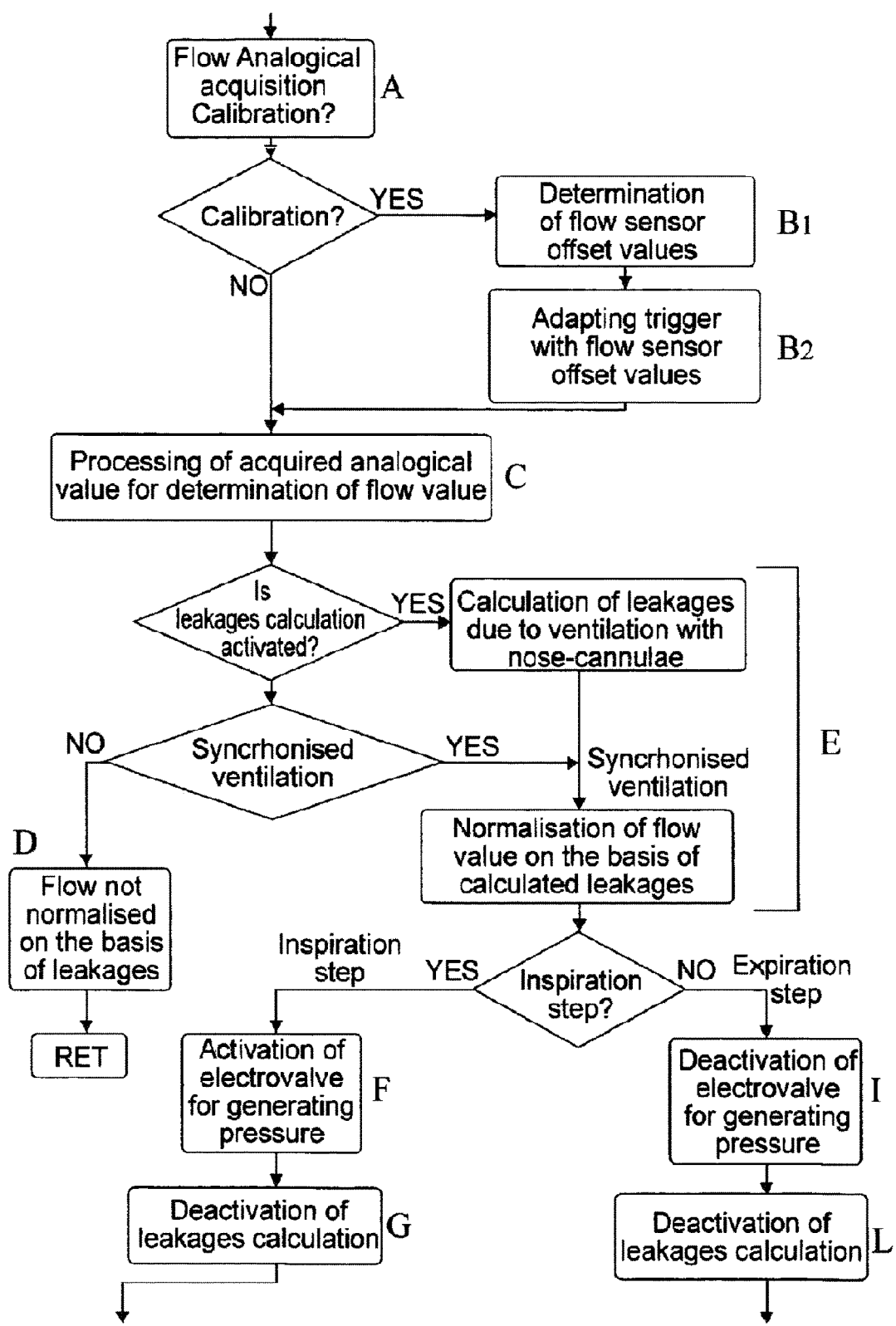
FIG. 1 shows a flow chart of a method for controlling nasal ventilation according to the present invention.
Figure 1B:
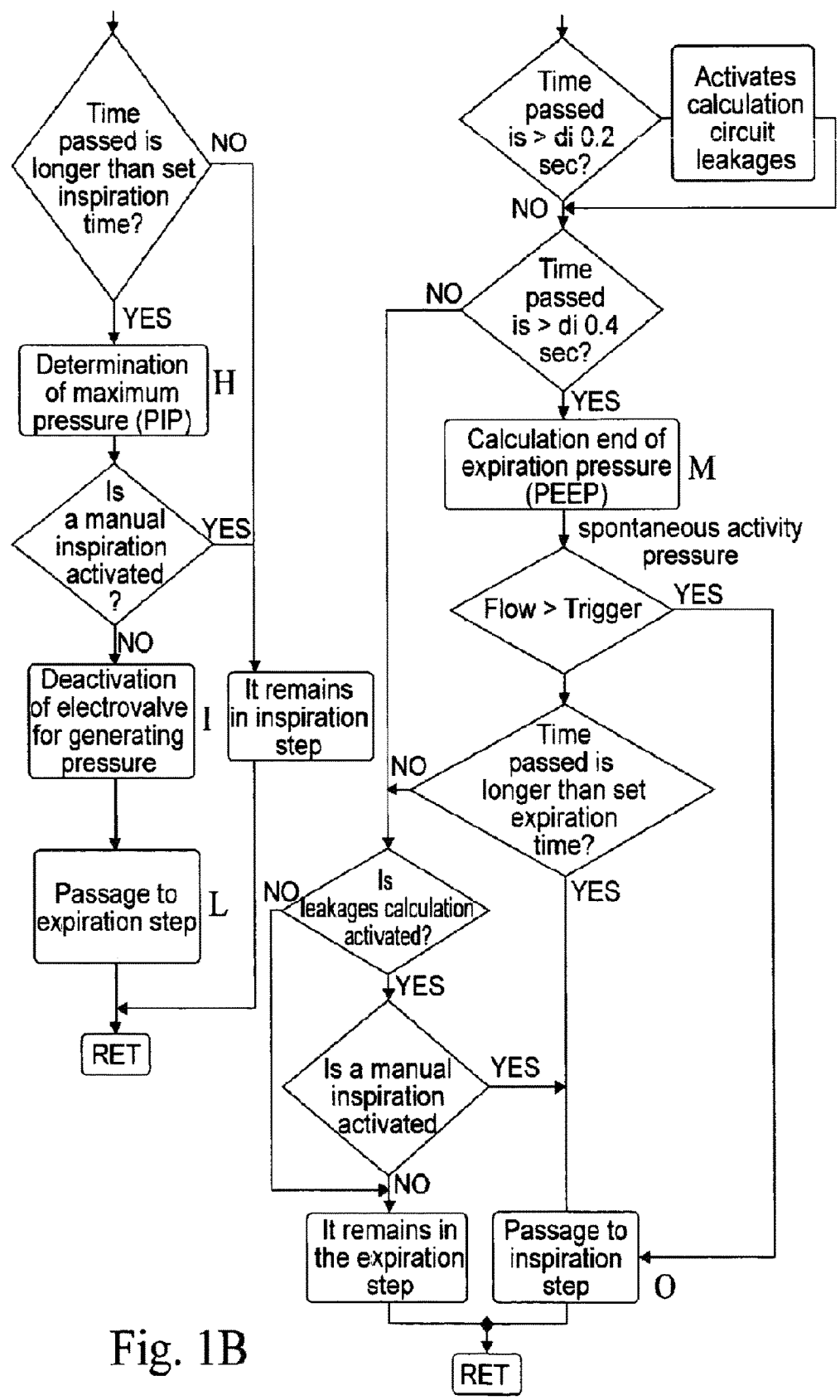

Making now reference to FIG. 1, it is possible observing a flow chart describing the whole operation of an apparatus for assisted respiration and providing the sub-procedure according to the present invention.

Following the flow chart, it is observed first a step A of analogical acquisition of the respiratory flow.

Then, procedure can provide carrying out calibration steps B' and B" in the first cycle.

In case said steps B' and B" must be carried out, a determination of offset and trigger signal values follows calibration values.

As it is well known, inspiration time Ti and expiration time Te are parameters set by the doctor, always within physiological intervals.

As mentioned in the above, critical detection consists in putting apparatus under conditions avoiding false signals of inspiration air flow. In fact, if a false signal would overcome trigger value threshold Tfr set by the doctor, air would be forced within new-born lungs when he/she does not need it.

Following step C provides analogical detection of air flow signal.

Obviously, in case synchronised ventilation would not be actuated, apparatus would not assist ventilation and would produce a not normalised flow, and thus not depurated from leakages when set by the doctor (step D), as it occurs in the common ventilation apparatuses according to the known art.

Instead, in case synchronised ventilation would be actuated, sub-procedure would start, calculating losses and normalisation E.

Figure 2:
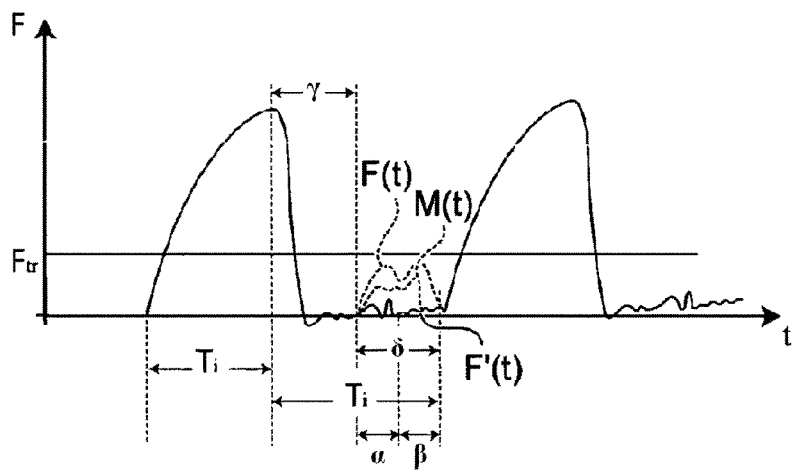
FIG. 2 shows a typical waveform of the respiratory flow signal in function of time, obtained during the method of FIG. 1.
Figure 3:
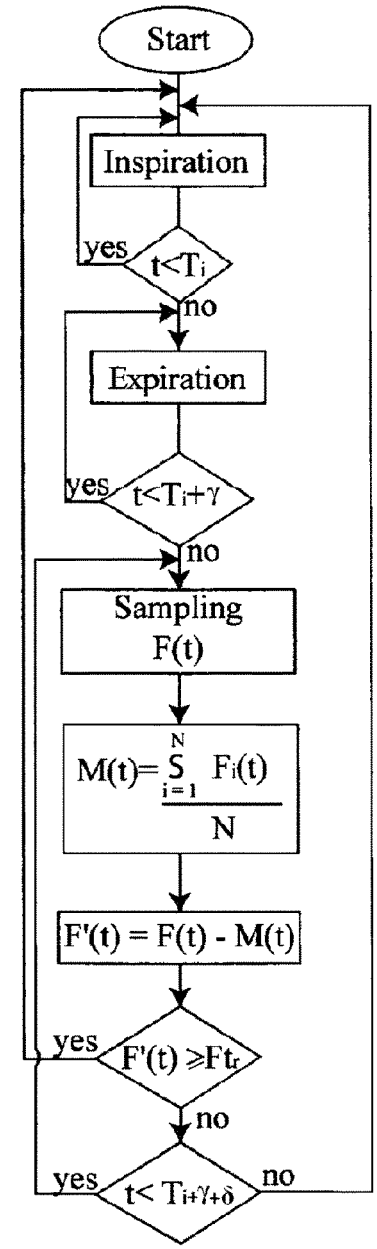
FIG. 3 shows procedure for calculating leakages and normalization according to the present invention.

Leakages calculation starts after a time γ is passed from the inspiration end. More specifically Ti+Te time defined in the above individuates total time for a respiratory cycle, as it can be observed from FIG. 2, showing a qualitative diagram obtained making an assisted respiration according to the inventive method. Then, in FIG. 3 it is possible observing in greater detail the sub-procedure for calculating leakages and normalisation during a total respiratory cycle.

Flow F(t) detected can be considered the sum of the outlet flow and of leakages of circuit within time interval Ti+γ<t<Ti+Te, instead patient expiration flow can be considered neglect able with respect to leakages, thus signal F(t) detected can be only attributed to the circuit leakages.

Leakages by which all signal F(t) is normalised obtaining signal F'(t) are calculated within time interval δ.

During time interval δ spontaneous respiration detection is also activated, i.e. if F'(t)≧Ftr, machine synchronises passing to a new inspiration step.

It is generally possible providing a further improvement of procedure, particularly, time interval δ can be divided into two further periods lasting α and β, respectively.

Said time interval α preferably lasts 0.2 seconds, and during said interval the sample detection step and average calculation step are started. Instead, real starting of the spontaneous respiration activation step occurs within the time interval β=δ−α. This permits increasing probability of avoiding wrong activation of assisted respiration, in any case facilitating respiratory activity.

The above normalisation step occurs as follows.

Sampling of N samples for each interval δ on flow signal F(t) is carried out during time interval δ. In the present embodiment, N=16 samples are detected and memorised.

A variable average M(t) is calculated in real time, varying on he basis of the sample collected. In other words, said average M(t) is calculated on the basis of the last N detected samples (even if included within a δ time interval of the previous respiration cycle). During acquisition of each new sample, M(t) is again calculated in real time. Eldest sample is excluded from the calculation and replaced by the new one. It is a data collection and processing mode wherein last data is taken for processing and the first one is eliminated (LIFO—Last In First Out).

In the present embodiment, M(T) variable average signal is obtained by the following formula:

$$M(t) = \frac{\sum_{i=1}^{N} F_i(t)}{N}$$

-continued $$\text{per } Ti+\gamma < t < Ti+Te$$

wherein i is index numbering samples of F(t).

obviously, it is possible using other kind of algorithms for calculating variable average, such as weighted averages giving higher percentage when calculating the average of the last samples.

M(t) variable average value is detracted from the flow signal F(t) in real time, obtaining a normalised signal F'(t):

$$F'=F(t)-M(t)$$

For each time t.

During time interval δ, or preferably β, as already said, procedure for assisted respiration activates only if signal F'(t) is higher than trigger threshold Ftr. This permits eliminating all disturbance signals due to circuit leakages.

Once terminated time interval δ, system usually activates an assisted respiration cycle, initiating a new inspiration step lasting Ti. Particularly, coming back to FIG. 1, electrovalve 1 is actuated (step F) and leakages calculation (step G) is deactivated.

At the end of inspiration interval Ti, maximum value of inspiration pressure (PIP) (step H).

In case a manual respiration is present, it is provided that procedure for calculating leakages is deactivated, passing to inspiration step.

In the present embodiment, during set interval β, also expiration step termination pressure is calculated (PEEP), i.e. after about 0.4 seconds, corresponding to the sum of times γ and α (step M), i.e. at the end of time interval α.

Figure 4:
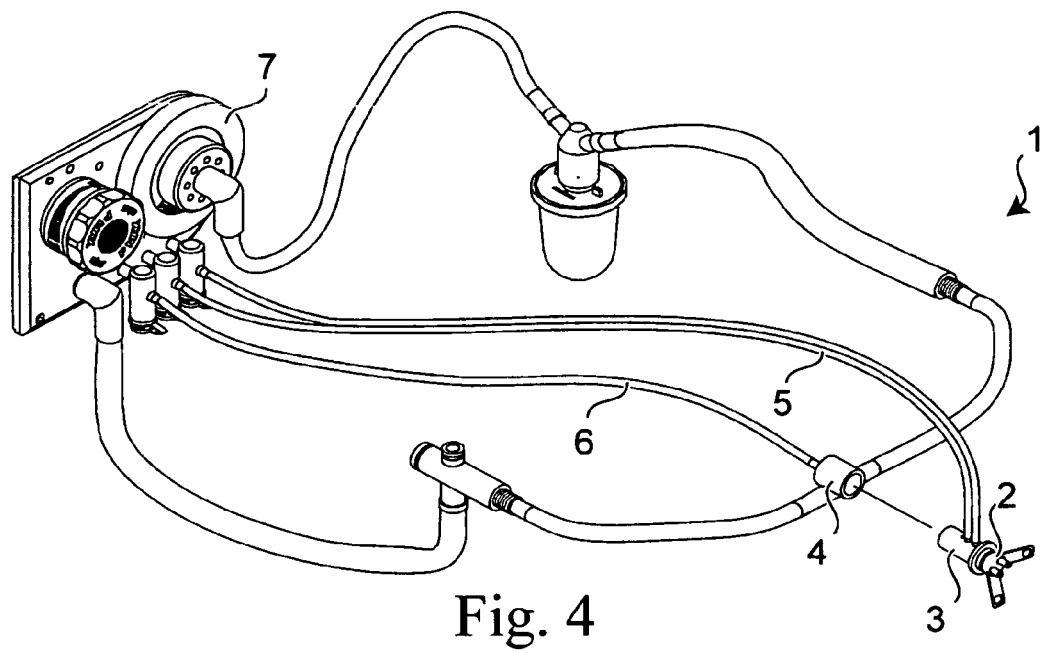
FIG. 4 shows ventilation circuit according to the invention of apparatus for carrying out method according to the present invention.

In FIG. 4 it is possible to observe a part of apparatus 1 for carrying out the method according to the invention. Particularly, it is observed a nose-cannula 2 applied to a pneumotachograph 3 that is applied to a traditional ventilation system by a connector 4. Tube 5 is used for detection of air flow, while tube 6 is suitable for detecting pressure.

Apparatus 1 provides also an electrovalve 7 for creating pressure inside the circuit.

Figure 5:
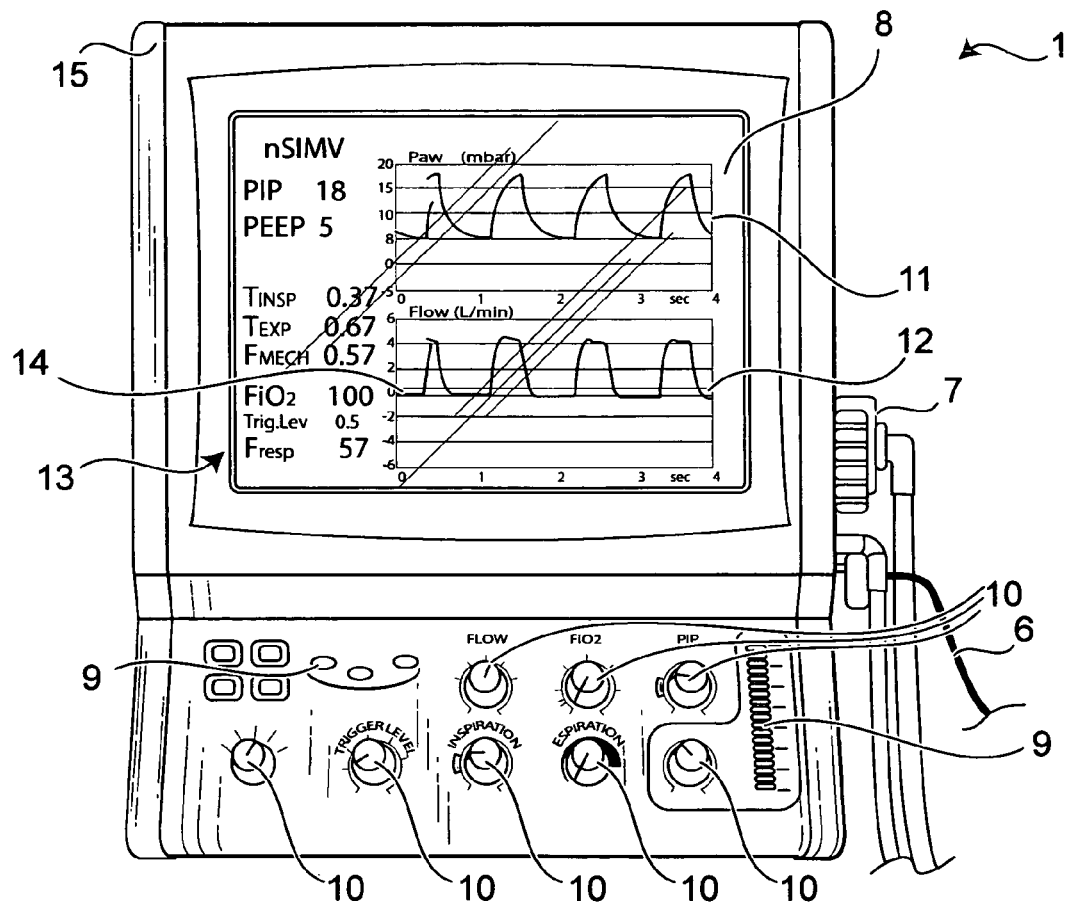
FIG. 5 shows interface means of apparatus for carrying out method according to the invention.

Making now reference to FIG. 5, it is possible observing interface means of apparatus 1. Said means comprise a monitor 8, light indicators 9 and a plurality of knobs 10. It is further provided an acoustic alarm, not shown in the figure.

Monitor 8 permits to medical or paramedic personnel monitoring respiration frequency. It is possible immediately knowing if new-born has frequent spontaneous activities, and therefore respiratory irregularities. In this case, doctor can modify respiratory parameters, or modify respiration mixture.

Video continuously shows pressure 11 and flow 12 graphs. Furthermore, value set by respiration adjustment knobs 10 are shown aside said graphs, such as Ti, Te, selected mixture, respiration frequency, trigger flow value, respiration peak pressure (PIP), expiration termination pressure (PEEP).

In case of anomalous operation, apparatus emits a sound signal permitting to medico personnel to immediately intervene.

Apparatus electronic control units are closed within a chassis 15.

On the basis of the above specification, it can be noted that the basic feature according to the present invention is that of estimating period during which it is possible calculating circuit leakages during expiration step, permitting a normalisation of flow signal preventing error signals.

A first advantage of the present invention is that of suggesting a procedure that can be easily implemented in a centralised control electronic system.

A second advantage of the present invention is that of permitting the use of the nose-cannula for assisted respiration in a much higher number of cases, also permitting the use of endotracheal intubation.

The present invention has been described for illustrative but not limitative purposes, according to its preferred embodiments, but it is to be understood that modifications and/or changes can be introduced by those skilled in the art without departing from the relevant scope as defined in the enclosed claims.

The invention claimed is:

1. A method, for flow-synchronized neonatal assisted ventilation, wherein F(t) is a signal proportional to the ventilation flow, comprising the following steps:
    (a) activating an electrovalve for inspiration, for a time length Ti, during which air is introduced at an inspiration pressure;
    (b) deactivating the electrovalve for expiration, for a time length Te, during which the introduction of air is interrupted; and
    (c) returning to step (a);
        during said expiration step (b) the following steps are provided:
    (b1) a waiting step having a non-zero time length γ before activation of computation of leakages in a ventilation circuit configured for a newborn; and
    (b2) a step of computation of the leakages, having a time length δ, so that γ+δ=Te, wherein when a normalized signal F'(t), obtained by processing said detected signal F(t) according to a normalizing algorithm, exceeds an expiration flow rate threshold Ftr, a spontaneous respiration activity is determined and the step (a) is reactivated,
    wherein said algorithm provides the following sub-steps:
        sampling of the F(t) signal;
        calculation of a variable average M(t) for each sample for Ti+γ<t<Ti+Te;
        calculation of F'(t) signal according to formula F'(t)=F(t)−M(t) (for each t value),
    wherein said variable average M(t) is calculated according to the following formula:

$$M(t) = \frac{\sum_{i=1}^{N} F_i(t)}{N} \text{ for } Ti + \gamma < t < Ti + Te,$$

wherein i is the index numbering F(t) samples; N is the number of samples used for calculation of leakages (b2), and,
    wherein calculation of average is carried out for each sample acquired during step (b2), inserting each time the new value acquired.

2. The method according to claim 1, wherein number N of said samples is 16.

3. The method according to claim 1, wherein step (b2) is divided into two further steps, during respectively α and β, so that γ=α+β:
    a first further waiting step;
    a second step for verifying presence of spontaneous activity, wherein when F'(t) passes threshold Ftr, inspiration step (a) is reactivated.

4. The method according to claim 1, wherein said time interval γ is in the range between 0.20 and 0.25 seconds.

5. The method according to claim 4, wherein said time interval γ is 0.20 seconds.

6. The method according to claim 3, wherein said time interval α is included in the range between 0.20 and 0.25 seconds.

7. The method according to claim 3, wherein said time interval a is 0.20 seconds.

8. The method according to claim 3, wherein in said method, during step b(2), if signal F'(t) takes value Ftr (with Ti+γ+α<t<Ti+γ+δ), inspiration step (a) can be reactivated.

9. The method according to claim 1, wherein during step (b2), within time interval δ it is possible to memorize the pressure at the end of expiration.

10. The method according to claim 1, wherein at the end of step (a), the maximum value of inspiration pressure is memorized.

11. The method according to claim 1, wherein said inspiration time interval is Ti.

12. The method according to claim 1, wherein said expiration time interval Te can be varied.

13. The method according to claim 1, wherein said Ftr threshold can be varied.

14. An apparatus for carrying out flow-synchronized neonatal assisted ventilation, said apparatus comprising:
    interface means, suitable to adjust operation parameters by a user,
    a circuit for nasal ventilation configured for a newborn,
    a pneumotachograph connected to said circuit and connected to flow tubes and pressure detection tubes, said pneumotachograph is configured to detect a signal F(t) proportional to the ventilation flow rate and to detect a plurality of parameters, said plurality of parameters comprise inspiration time Ti, expiration time Te, expiration flow threshold Ftr and respiration frequency, wherein said circuit for nasal ventilation comprises a nose-cannula connected with said pneumotachograph,
    an electrovalve connected with said circuit for nasal respiration for activating—deactivating the introduction of air at an inspiration pressure through said circuit for nasal respiration, and
    a processing and control unit, connected to said electrovalve and configured to control said electrovalve for activation during inspiration and deactivation during expiration, said deactivation including a waiting step having a non-zero time length γ,
    wherein the signal F(t) detected by the pneumotacograph is sampled,
    wherein said processing and control unit is provided with processing means that activates said electrovalve for inspiration, for the time Ti, during which air is introduced at an inspiration pressure, deactivating said electrovalve for expiration, for the time Te, during which the introduction of air is interrupted,
    wherein said processing means is configured to carry out the following electrovalve control:
    waiting a time length g; and
    computation of the leakages, having a time length d, so that g+d=Te, in which when a normalized signal F'(t), obtained by processing said detected signal F(t), exceeds said expiration flow rate threshold Ftr, a spontaneous respiration activity is determined and the activation of the electrovalve for inspiration is reactivated,
    said normalized signal F'(t) being calculated for each sample for Ti+g<t<Ti+Te, according to the formula F'(t)

=F(t)−M(t) (for each t value), where M(t) is a variable average M(t), calculated according to the following formula:

$$M(t) = \frac{\sum_{i=1}^{N} F_i(t)}{N} \text{ for } Ti + \gamma < t < Ti + Te,$$

for Ti+γ<t<Ti+Te,
wherein i is the index numbering F(t) samples and N is the number of samples used for calculation of leakages.

15. The apparatus according to claim 14, further comprising memorisation means.

16. The apparatus according to claim 14, wherein, said interface means including a monitor.

17. The apparatus according to claim 14, wherein said interface means comprise a push-button panel.

18. The apparatus according to claim 14, wherein said interface means comprise a plurality of knobs.

19. The apparatus according to claim 14, wherein said interface means further comprise at least one of a plurality of optical warning devices and acoustic warning devices.

20. The apparatus according to claim 14, wherein said apparatus further comprise means for adjustment of respiration mixture.

21. An apparatus for nasal ventilation, for flow-synchronized neonatal assisted ventilation, comprising:
a circuit for nasal ventilation, configured to be applied to a newborn;
an electrovalve connected with said circuit for nasal ventilation, for activating—deactivating the introduction of air at an inspiration pressure through said circuit for nasal ventilation;
a pneumotachograph, connected to flow tubes and pressure detection tubes, suitable to detect a signal F(t) proportional to the ventilation flow rate and a plurality of parameters, said parameters comprise inspiration time Ti, expiration time Te, expiration flow threshold Ftr and respiration frequency, said circuit for nasal ventilation comprises a nose-cannula connected with said pneumotachograph; and
a processing and control unit, connected to said electrovalve and said pneumotachograph, adapted to control said electrovalve, said processing and control unit being configured to:

(a) activate said electrovalve for inspiration, for a time length Ti, during which air is introduced at an inspiration pressure;
(b) deactivate said electrovalve for expiration, for a time length Te, during which the introduction of air is interrupted; and then to return to activating said electrovalve for inspiration;
said (b) includes:
(b1) a wait having a time length γ; and
(b2) a computation of leakages, having a time length δ, so that γ+δ=Te, in which when a normalized signal F'(t), obtained by processing said detected signal F(t) according to a normalizing algorithm, exceeds an expiration flow rate threshold Ftr, a spontaneous respiration activity is determined and wherein said processing and control unit is provided with processing means that activate said electrovalve for inspiration, for the time Ti, during which air is introduced at an inspiration pressure, deactivating said electrovalve for expiration, for the time Te, during which the introduction of air is interrupted,
wherein said processing means carry out the following electrovalve control:
waiting a time length g; and
computation of the leakages, having a time length d, so that g+d=Te, in which when a normalized signal F'(t), obtained by processing said detected signal F(t), exceeds said expiration flow rate threshold Ftr, a spontaneous respiration activity is determined and the activation of the electrovalve for inspiration is reactivated,
said normalized signal F'(t) being calculated for each sample for Ti+g<t<Ti+Te, according to the formula F'(t) =F(t)−M(t) (for each t value), where M(t) is a variable average M(t), calculated according to the following formula:

$$M(t) = \frac{\sum_{i=1}^{N} F_i(t)}{N}$$

per $Ti + \gamma < t < Ti + Te,$ wherein i is the index numbering F(t) samples and N is the number of samples used for calculation of leakages.

* * * * *